United States Patent [19]

Lemay

[11] Patent Number: 4,670,611
[45] Date of Patent: Jun. 2, 1987

[54] METHOD AND INSTALLATION FOR THE CRYSTALLIZATION OF MANNITOL

[75] Inventor: Patrick Lemay, Lestrem, France

[73] Assignee: Roquette Freres, Lestrem, France

[21] Appl. No.: 863,014

[22] Filed: May 14, 1986

[30] Foreign Application Priority Data

May 15, 1985 [FR] France .................................. 85 07428

[51] Int. Cl.⁴ ........................ C07C 29/78; C07C 31/26
[52] U.S. Cl. ..................................... 568/868; 422/245
[58] Field of Search .......................................... 568/868

[56] References Cited

U.S. PATENT DOCUMENTS

| 2,315,699 | 4/1943 | Goepp ................................. 568/868 |
| 2,594,863 | 4/1952 | Buck et al. .......................... 568/868 |
| 3,330,874 | 7/1967 | Shannon ............................. 568/868 |
| 3,632,656 | 1/1972 | Unver ................................. 568/868 |

FOREIGN PATENT DOCUMENTS

| 37711 | 7/1973 | Australia . |
| 554859 | 3/1958 | Canada ............................... 568/868 |
| 16085 | 5/1977 | Japan .................................. 568/868 |
| 1481846 | 8/1977 | United Kingdom ............... 568/868 |

Primary Examiner—J. E. Evans
Attorney, Agent, or Firm—Larson and Taylor

[57] ABSTRACT

A syrup of mannitol and of sorbitol is introduced through a pipe (2) into a first crystallization zone (1a) which it is led to pass through with stirring (3) and within which the temperature is maintained substantially constant by a system (4), the mixture of syrup and of crystals of mannitol being led through a pipe (8) to a second crystallization zone (1b) which it is led to pass through and within which it is subjected to a temperature gradient decreasing globally possibly modulated by a system of temperature regulation (12), the mixture emerging from this second zone being in the form of a crystalline mass rich in mannitol crystals from which the latter are recovered. A system of recycling (13) leads, in the vicinity of the upper end of the container (1a), a part of the contents of the container (1b) taken up to a level (15).

10 Claims, 1 Drawing Figure

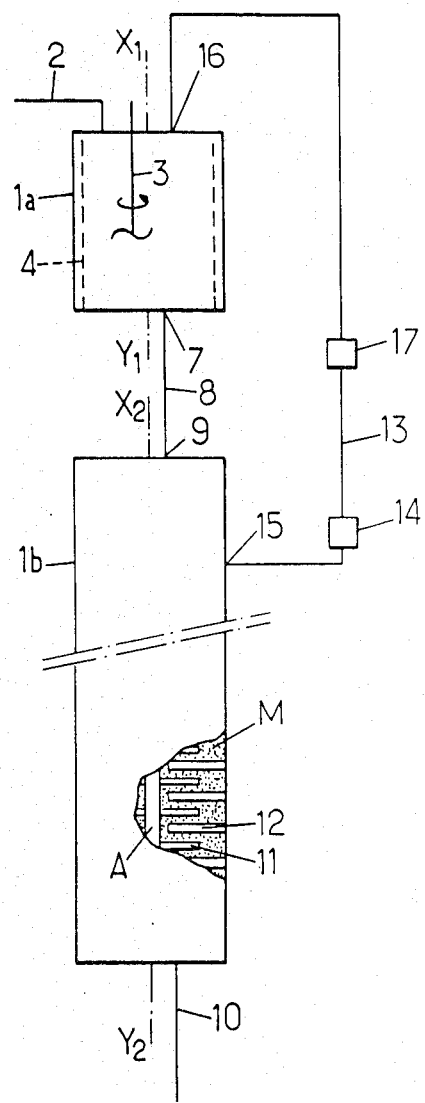

METHOD AND INSTALLATION FOR THE CRYSTALLIZATION OF MANNITOL

The invention relates to a method and to an installation for the crystallization of mannitol.

It is known, particularly through U.S. Pat. No. 3,632,656, to prepare crystalline mannitol from aqueous solutions rich in mannitol and in sorbitol in the presence of mannitol crystals which play the role of crystallization seeds. The crystallization is performed according to this U.S. patent in a vertical crystallizer provided with means for stirring and regulation of the temperature adapted to maintain within the mixture of syrup and of crystals a constant temperature of the mannitol, the dwell time of a given fraction of mixture inside the crystallizer being from 2 to 15 hours.

Known methods do not give entire satisfaction either from the point of view of productivity per unit volume of equipment or that of the energy balance.

Now, in order to face up to the requirements, particularly in the economic field, which are constantly more severe, the Applicants have sought to develop a method and an installation responding better than those already existing, to the various desiderata of the practice, in particular precisely from the point of view of the productivity of the crystallization operation per unit volume of the equipment used and the energy balance.

And they have found that this object could be achieved by a method of continuous crystallization of the mannitol, characterized by the fact that a syrup of mannitol and of sorbitol, preferably free from mannitol crystals and nuclei, of a richness in mannitol higher than 20%, preferably comprised between 20 and 50%, more preferably between 30 and 45% and still more preferably between 35 and 42%, of a content of dry matter from 60 to 90%, preferably from 60 to 85% and at a temperature of 70° to 100° C., is introduced into a first crystallization zone of axis preferably substantially vertical which it is brought to traverse under stirring and within which there is maintained a substantially constant temperature, less by 3° to 30° C., preferably by 3° to 25° C. and more preferably by 3° to 20° C. than the saturation temperature, due to which the initiation of crystallization occurs which is manifested by the formation of a mixture of syrup and of crystals of mannitol, the average dwell time of a given fraction of mixture inside the first zone being from 10 to 35 hours, preferably from 15 to 20 hours, so that this mixture emerging from the said first zone shows a concentration of crystals of 5 to 20%, said mixture emerging from the first zone being brought to traverse, from top to bottom, with malaxation, a second crystallization zone of preferably substantially vertical axis arranged preferably substantially in extension of that of the first zone, a temperature gradient globally decreasing possibly modulated from 0.5° to 2° C./hour, preferably from 1° to 1.5° C./hour, being imposed inside this second zone on the mixture which transverses it, the temperature in the vicinity of the upper end of the second zone being preferably close to the temperature existing in the first zone, the mixture which emerges from the second zone being in the form of a crystalline mass rich in mannitol crystals from which the latter are recovered, the initiation of crystallization at the level of the first zone being facilitated by the recycling preferably to the level of the upper end of the latter of a fraction of the mixture passing through the second zone, which fraction represents from 10 to 120%, preferably from 40 to 110% and still more preferably from 80 to 100% of the amount of syrup introduced into the first zone, this fraction, which is taken up at a level spaced from the ends of the second zone by at least one sixth of the total height and preferably situated in the upper part of the second zone, particularly between one sixth and one half of its total height, being advantageously subjected to a fragmentation of the crystals that it contains, before its introduction preferably at the level of the upper end of the first zone.

To carry out the abovesaid method, recourse is had, according to the invention, to an installation comprising essentially two containers of preferably substantially vertical axes arranged preferably one above the other, the axes of the two containers being preferably substantially in extension of one another, the first container, or container for initiation crystallization, being equipped on the one hand with a feed system for syrup rich in mannitol in the vicinity of its upper end, on the other hand with a stirring system for the contents of the container and a system for regulating the temperature adapted to establish inside the container a substantially constant temperature at all points and finally with an extraction system arranged in the vicinity of its lower end, this system being adapted to withdraw the mixture of syrup and of crystals formed inside the container and to lead this mixture to a point situated in the vicinity of the upper end of the second container, or container of crystallization proper which is equipped with a malaxation system for the contents and with a system for regulation of temperature adapted to establish within the mass subject to crystallization which fills it an overall temperature gradient decreasing from top to bottom, the said second container being furthermore equipped, in the vicinity of its lower end, with a continuous extraction system for a product highly enriched in mannitol crystals which is led by suitable means to a system permitting recovery of the mannitol crystals from this product, said installation being in addition equipped with a system for recycling to a point situated preferably in the vicinity of the upper end of the first container of a portion of the contents of the second container taken up at a level of the second container corresponding to a point spaced from the ends of the second zone by at least one sixth of the total height and preferably situated in the upper part of the second container, particularly between one sixth and one half of its total height, said system of recycling comprising advantageously means for fractionating the crystals contained in the recycled mass.

The invention is also directed at other features which are preferably used at the same time and which will be more explicitly discussed below.

And it will, in any case, be well understood by means of the additional description which follows and the accompanying drawing which relate to advantageous embodiments.

The single figure of the drawing shows diagramatically an installation according to the invention.

Consequently, in order to prepare crystalline mannitol according to the invention, procedure is as follows or in equivalent manner.

As raw material, a syrup rich in mannitol is used, preferably free from crystals and from nuclei, coming for example from the hydrogenation of syrups rich in fructose; this syrup has a content of dry matter of about 60 to 90% by weight, preferably from 60 to 85% by weight, the mannitol constituting at least 20%, preferably 20 to 50%, more preferably 30 to 45% and still more preferably 35 to 42% by weight on dry matter of this syrup.

This concentrated syrup is brought to a first crystallization zone of axis preferably substantially vertical, which it traverses continuously under stirring and within which there is maintained a substantially constant temperature, below the temperature of saturation, particularly from 3° to 30° C., preferably from 3° to 25° C. and still more preferably from 3° to 20° C., due to which there is produced the initiation of the crystallization which is manifested by the formation of a mixture of syrup and of mannitol crystals.

The average dwell time of a given fraction of mixture inside this first zone is from 10 to 35 hours, preferably from 15 to 20 hours, so that the mixture emerging from the container has a concentration of crystals of 5 to 20%.

The mixture emerging from the first zone is then led to traverse from top to bottom, with malaxation, a second crystallization zone of axis preferably substantially vertical, arranged preferably in extension of that of the first zone.

The temperature of the mixture is maintained, preferably, at the moment of its introduction into the second crystallization zone, at a value close to that which exists inside the first zone.

A temperature gradient, globally decreasing from top to bottom, of 0.5° C. to 2° C./hour, preferably from 1° to 1.5° C., is imposed on the mixture, that is to say on the mass subject to crystallization which traverses this second zone.

The mixture emerging from the second zone is in the form of a crystalline mass rich in mannitol crystals, from which these crystals are recovered.

The richness of this mass with respect to mannitol crystals is 17 to 45%.

The whole of the mass filling the second crystallization zone traverses the latter in the manner of a "piston", the term used in the art.

The starting of crystallization at the level of the first zone is facilitated by the recycling to the level of preferably the upper end of the latter, of a fraction of the mixture passing through the second zone, this recycled fraction representing from 10 to 120%, preferably 40 to 110% and more preferably from 80 to 100% of the syrup not containing nuclei introduced into the first zone.

This fraction is taken up at a level spaced from the ends of the second zone by at least one sixth of the total height and preferably situated in the upper part of the second zone, particularly between one sixth and one half of its total height.

The recycled fraction is in addition subjected, preferably, to a fractionation of the crystals that it contains, before its introduction at the level at the upper end of the first zone.

Due to the method according to the invention, there is extracted continuously, in the vicinity of the lower end of the second crystallization zone, a mass rich in mannitol crystals without the occurrence of disturbances of the parameters of the crystallation process, which disturbances have repercussions at the level of the following separation step of the liquid phase and of the crystals and which could necessitate intermittent stoppages of the installation. In other words, this method enables a very favorable productivity to be arrived at per unit volume of the equipment used for the practising of the method.

This productivity is higher than that obtained in the methods of the prior art.

The feed flow rate in mannitol rich syrup is selected so that the average dwell time, of a given fraction of the mass subjected to crystallization inside the second crystallization zone is from 25 to 90 hours, preferably from 30 to 50 hours; the value selected depends on the thermal exchange capacities of the means comprised by this second zone and by means of which there is established, within said zone in the mass subjected to crystallization, the decreasing temperature gradient which was considered above.

The viscosity of the mass subjected to crystallization which is increased progressively as the proportion of mannitol crystals grows, that is to say in the descending sense, is the reason for which the crystallization zone is, preferably, equipped with discharging or aspiration means adapted to facilitate the conduction of the mass inside the zone.

In addition, the means of malaxation and of homogenization comprised by the second crystallization zone must be arranged so that dead zones are avoided and so that the heat exchange between the mass subjected to crystallization and the cooling means is as effective as possible.

The product extracted from the second crystallization zone and which constitutes, as already indicated, a mass rich in mannitol crystals, comprises crystals of mannitol with a granulometric spectrum characterized by a low proportion of fines and coarse crystals and hence by a high proportion of crystals of intermediate size, this spectrum not varying over time, due to which the following treatment step, which consists of separating these crystals from the liquid phase in which they are contained, is not subject to disturbance.

This separation comprises a centrifugal draining treatment and possibly washing due to which the major part of the liquid phase is recovered; the latter forms mother liquors whose concentration in mannitol is less than that of the starting mannitol-rich syrup—this concentration generally reaches from 7 to 15%—and in which is to be found again almost the whole of the sorbitol and the impurities contained in said starting syrup.

According to the crystallographic nature of the mannitol crystals, of the type $\alpha$, $\beta$ or $\delta$ used for initiation at the level of the first zone, there is obtained at the end of the operation a crystalline mannitol of the same crystallographic nature, namely respectively of the type $\alpha$, $\beta$ or $\delta$.

It is possible that the globally decreasing temperature gradient imposed on the mass subject to crystallization which traverses the second zone is modulated, i.e. comprises for instance a first part wherein it is really decreasing and a second part wherein temperature is constant, the part of the second zone which corresponds to this second part of the gradient playing practically the role of a ripening zone.

Now, in order to carry out the method according to the invention, recourse may be had to the installation which will now be discussed.

This installation comprises essentially two containers $1a$ and $1b$ advantageously arranged one ($1a$) above the other ($1b$); these containers have advantageously the shape of cylinders of revolution with axes $X_1$, $Y_1$ and X$_2$, Y$_2$ preferably substantially vertical and preferably situated in the extension of one another.

The container 1a is equipped with a mannitol rich syrup feed system at the level of its upper end and shown diagrammatically by a pipe 2, with a stirring system 3 and with a system for the regulation of the temperature shown diagrammatically at 4 and adapted to establish a temperature substantially constant at all points inside the container.

The mixture constituted of mannitol syrup and mannitol crystals which is formed inside the container 1a, flows from the latter at a point 7 situated in the vicinity of the lower end of this container: at this point the container may comprise a pipe 8 through which the mixture is led to the container 1b; it may also be provided for the outlet orifice from the container 1a to be positioned facing the input orifice of the container 1b, the two containers then being juxtaposed.

As a general rule, it is however the arrangement shown in the figure which is adopted, the two containers being arranged, one beneath the other preferably in extension of one another, the pipe 8 playing simultaneously the role of extraction pipe for the container 1a and feed pipe for the mixture of mannitol syrup and mannitol crystals for the container 1b at a point 9 of the latter close to its upper end.

The container 1b is equipped with a system of malaxation and of regulation of temperature which will be discussed and with a system for continuous extraction at the level of the lower end of the container and shown diagrammatically by pipe 10, this system being adapted to recover the mass rich in mannitol crystals obtained at the outlet of the container 1b.

The system for malaxation and regulation of temperature which is mentioned above can advantageously comprise a group of malaxation arms 11 borne at regular intervals by a rotary shaft A whose axis is merged with the axis X$_2$Y$_2$ of the container 1b, cooling layers 12 arranged in alternation with the malaxation arms 11 and borne by the wall of the container 1b, these cooling layers being traversed by a cooling fluid.

The system of temperature regulation is arranged so that it permits the establishment inside the container 1b, of an overall temperature gradient decreasing downwards.

The container 1b comprises in addition means globally represented by a pipe 13 comprising a pump 14 and adapted to take up at level 15 spaced from the ends of the second zone by at least one sixth of the total height and preferably situated in the upper part of the second zone, particularly between one sixth and one half of its total height, a fraction of the mass M subjected to crystallization and passing through the container 1b and to recycle this fraction to a level 16 situated in the vicinity of the upper end of the container 1a.

Preferably, the pipe 13 comprises fragmentation means 17, for example a grinder, adapted to disaggregate the biggest crystals and possible aggregates of mannitol crystals contained in the recycled fraction.

The thermal exchange capacity of the system of temperature regulation, the rotary speed of the malaxation means and the speed with which, under the influence of aspiration means (not shown), the mass subjected to crystallization passes through the container, that is to say the average dwell time of a given fraction of this mass inside the container, are selected so that there is established, in the whole of the mass subjected to crystallization, the abovesaid temperature gradient.

It is pointed out that, in practice, the cooling fluid is water and that the average difference in temperature a given point of the container between this water and the mass subjected to crystallization, is of the order of 2° to 15° C.

EXAMPLE (a) Recourse is had to an installation according to the invention comprising two cylindrical containers 1a and 1b of respective useful volumes of 1.350 and 3.3 m$^3$.

There is introduced into the container 1a, with a flow rate of 90 l per hour, a syrup of mannitol and of sorbitol having a content of sugar dry matter of 78% and comprising 40.5% by weight to dry matter of mannitol, the remaining 59.5% being constituted particularly by sorbitol and hydrogenated polysaccharides.

The temperature of the syrup at the inlet of the container 1a is about 90° C., the temperature in the container being 68° C.

To start up the crystallization process, there is introduced, at the level of the upper part of the container 1a, a seed constituted by mannitol of type β.

The average dwell time inside the container 1a of a given fraction of the mixture of syrup and of mannitol crystals is about 15 hours.

At the outlet of the container, this mixture shows a concentration of crystals of about 8% with respect to the dry matter.

The mixture emerging from the container 1a is led through the pipe 8 at a point 9 of the container 1b situated in the vicinity of the upper end of the latter.

Inside the container 1b, this mixture is subjected to a temperature gradient decreasing overall by 1.3° C./hour; the top temperature of this gradient is 68° C. and the bottom temperature 20° C.

At the level of the point 15 situated at a third of the total height from the upper end of the container 1b, is taken up a fraction of the mass subjected to crystallization which passes through it and this fraction is recycled to a point located preferably in the vicinity of the upper end of the container 1a at 16, the crystal aggregates having been broken before.

The recycled fraction corresponds to 100% of the amount of syrup introduced through the pipe 2.

The mass rich in crystals of mannitol of type β withdrawn at the level of the lower end of the container 1b through the pipe 10 is at a temperature in the vicinity of 20° C. and permits the separation of an amount of crystals corresponding by weight to 32% of the mixture.

The separation of the mannitol crystals is effected by centrifugal draining, then the crystals are washed.

The content of mannitol of the mother liquors recovered is 12% of dry matter and reaches 18% after washing of the crystals.

The crystallization yield which is given by the formula:

$$r = A - H/100 - H$$

in which

A, which represents the richness in mannitol of the feed syrup, is equal to 40.5% and H, which represents the richness of the mother liquors in mannitol, is 18% after washing, is established at 27.5%.

In this way there is produced daily 625 kg of mannitol of type β, which corresponds to a productivity of 189 kg daily and per m³ of the crystallization container.

In addition, no disturbance necessitating the stoppage of the installation occurs, which operates continuously.

The crystals collected after centrifugal draining and washing show excellent physical and chemical properties.

These crystals are of a purity at least equal to 98%.

(b) The same equipment and the same operational conditions are used.

However, at a given moment, after having reached the equilibrium of the system, the recycled fraction is taken up at a level situated outside the range according to the invention.

There is then rapidly witnessed a development of the parameters of the crystallization which is manifested after some hours by poor separation at the level of the centrifuges and which finishes by necessitating the stoppage of the installation and the removal of the mass that it contains before starting up again under the conditions according to the invention.

As is self-evident and as emerges besides already from the foregoing, the invention is in no way limited to those of its types of application and embodiments which have been more particularly envisaged; it encompasses, on the contrary, especially, on the one hand, the case according to which the installation according to the invention comprises a single container inside which there is materialized by way of adapted means the zones of starting of crystallization (first zone), of crystallization proper (second zone) and of ripening, on the other hand, the case according to which the installation according to the invention comprises the first container (starting of the crystallization) and the second container (crystallization proper) as disclosed in the specification, the ripening zone being materialized by a third container independent from the two preceding ones and situated in their extension, the said third container comprising means proper to impose a constant temperature on the mass by which it is traversed and which is coming from the second container.

I claim:

1. Method for the continuous crystallization of mannitol characterized by the fact that a syrup of mannitol and of sorbitol, of a richness in mannitol higher than 20%, of a concentration of dry matter of 60 to 90% and of a temperature of 70° to 100° C., is introduced into a first crystallization zone of axis substantially vertical, that it is led to pass through with stirring and inside which it is maintained at a substantially constant temperature, less by 3° to 30° C., than the saturation temperature, due to which there is produced the starting or initiating of the crystallization which is manifested by the formation of a mixture of syrup and of crystals of mannitol, the average dwell time of a given fraction of mixture inside that first zone being from 10 to 35 hours, so that this mixture emerging from the said first zone has a concentration of crystals of 5 to 20%, said mixture emerging from the first zone being led to pass through, from top to bottom, under malaxation, a second crystallization zone of axis substantially vertical, arranged substantially in extension of that of the first zone, a temperature gradient globally decreasing of 0.5° to 2° C./hour, being imposed inside this second zone on the mixture which passes through it, the temperature in the vicinity of the higher end of the second zone being close to the temperature inside the first zone, the mixture which emerges from the second zone being in the form of a crystalline mass rich in mannitol crystals from which the latter are recovered, the starting of the crystallization at the level of the first zone being facilitated by the recycling at the level of the upper end of the latter of a fraction of the mixture passing through the second zone, which fraction represents from 10 to 120%, of the amount of syrup introduced into the first zone, this fraction being taken up at a level spaced from the ends of the said second zone by at least one sixth of its total height.

2. Method according to claim 1, characterized by the fact that the richness in mannitol of the syrup feeding the first zone is comprised between 20 and 50%.

3. Method according to claim 1, characterized by the fact that the recycled fraction is taken up at a level situated in the upper half of the second zone between 1/6 and the middle of the total height of this second zone.

4. Method according to claim 1, characterized by the fact that the recycled fraction is subjected to fragmentation of the crystals that it contains, before its introduction into the first zone.

5. Method according to claim 1, characterized by the fact that the globally decreasing gradient imposed to the mass subject to crystallization and traversing the second zone comprises a first part within which it is actually decreasing, the second part of the second zone within which temperature is then substantially constant constituting a ripening zone.

6. Method according to claim 1 wherein the syrup is maintained in the first crystallization zone at a substantially constant temperature less by 5° to 25° C. than the saturation temperatures, the average dwell time in the first crystallization zone is from 15 to 20 hours, the temperature gradient globally decreasing in the second crystallization zone is 1° to 1.5° C./hour and the fraction recycled represents 40 to 110% of the amount of syrup introduced into the first zone.

7. Method according to claim 1 wherein the temperature gradient globally decreasing is modulated.

8. Method according to claim 6 wherein the syrup is maintained in the first crystallization zone at a substantially constant temperature less by 3° to 20° C. than the saturation temperature and the fraction recycled represents 80 to 100% of the amount of syrup introduced into the first zone.

9. Method according to claim 2 wherein the richness in mannitol of the syrup feeding the first zone is comprised between 30 and 45%.

10. Method according to claim 2 wherein the richness in mannitol of the syrup feeding the first zone is comprised between 35 and 42%.

* * * * *